(12) United States Patent
Spiegl

(10) Patent No.: US 8,408,048 B2
(45) Date of Patent: Apr. 2, 2013

(54) SOFT WATER MONITORING APPARATUS

(75) Inventor: Peter Spiegl, Aidlingen (DE)

(73) Assignee: Karl Spiegl, GmbH & Co., Magstadt (DE)

( * ) Notice: Subject to any disclaimer, the term of this patent is extended or adjusted under 35 U.S.C. 154(b) by 390 days.

(21) Appl. No.: 12/719,066

(22) Filed: Mar. 8, 2010

(65) Prior Publication Data
US 2011/0214492 A1    Sep. 8, 2011

(51) Int. Cl.
*G01N 11/00* (2006.01)
(52) U.S. Cl. .................................................. 73/53.01
(58) Field of Classification Search ............... 73/64.56, 73/60.11, 53.01, 61.41; 210/687
See application file for complete search history.

(56) References Cited

U.S. PATENT DOCUMENTS
6,926,835 B2 * 8/2005 Iizuka et al. .................. 210/662

FOREIGN PATENT DOCUMENTS
DE    3406724 C2    10/1985
EP    0016408 A1    10/1980

* cited by examiner

*Primary Examiner* — Peter Macchiarolo
*Assistant Examiner* — Jamar Ray
(74) *Attorney, Agent, or Firm* — Brinks Hofer Gilson & Lione

(57) ABSTRACT

The present disclosure relates to an apparatus for monitoring the soft water conducted in a main flow, which includes a hardness measuring cell, a first secondary flow line branching off from the main flow and leading to the hardness measuring cell, and a second secondary flow line leading away from the hardness measuring cell and feeding into the main flow, wherein the two secondary flow lines and the hardness measuring cell are connected to a multiway valve.

7 Claims, 2 Drawing Sheets

SOFT WATER MONITORING APPARATUS

FIELD

The disclosure relates to an apparatus for monitoring soft water conducted in a main flow.

BACKGROUND

A soft water monitoring apparatus is used to monitor a soft water flow as to the hardness thereof and to protect the user of the soft water from excessively high water hardness. Some applications include steam boilers and reverse osmosis systems, evaporators and distillation systems. The system enables continuous monitoring.

A partial flow of the soft water is conducted through a hardness measuring cell during soft water monitoring. If hard water flows through the hardness measuring cell, the measurement filling in the hardness measuring cell is depleted and the volume thereof changes and shrinks. This causes an electrical signal to be triggered and a controller reports an alarm, which can be used to deactivate devices.

If the soft water supply is restored, the hardness measuring cell must be regenerated. Valves installed for this purpose over the measuring distance must be actuated and the measuring distance is disconnected in this way from the main flow. A small amount of brine is injected into the hardness measuring cell. The hardness measuring cell is then rinsed with soft water. This procedure lasts a total of 3 to 5 minutes. Hardness measuring cells are known, for example, from DE 34 06 724 C2 and from EP 0 016 408 A1. This process is carried out manually, which is not only laborious, but also time consuming.

SUMMARY

The present disclosure provides systems with a more user-friendly design. This is achieved in that the two secondary flow lines and the hardness measuring cell are connected to a multiway valve.

In the apparatus according to the present disclosure, each secondary flow line must no longer be individually decoupled from the main flow when the hardness measuring cell must be regenerated, but instead the secondary flow lines are jointly disconnected from the main flow, which can be carried out considerably faster. This decoupling is therefore particularly important, since the brine required for regeneration must not reach the main flow. The decoupling and connection of the secondary flow lines and the hardness measuring cell take place in a simple way according to the present disclosure by means of a multiway valve.

If this multiway valve is connected to a drive, the connection and disconnection of the secondary flow lines can be controlled remotely by means of a specific actuation of this drive, that is to say, no manual actuation of the system is necessary for this purpose.

The multiway valve is a 7/3 valve having seven connections and three switching positions in a further development of the present disclosure. The two secondary flow lines are connected to two connections of this multiway valve, wherein two further connections are assigned to the inlet and outlet of the hardness measuring cell.

A water jet pump is additionally connected to the multiway valve in a further development of the present disclosure. Two connections of the multiway valve are connected to the pressure connection and the suction connection of the water jet pump. The mouth of the water jet pump leads directly into a wastewater line.

The multiway valve is connected to a brine tank in a further development of the present disclosure. The brine required for regeneration reaches the circuit via the seventh connection of the multiway valve and can be fed to the hardness measuring cell with suitable switching of the multiway valve.

A flow governor is provided according to the present disclosure in the main flow and between the branchings of the secondary flow lines in order to ensure that a secondary flow flows through the hardness measuring cell.

A pressure difference in the flow of the soft water through the measuring distance and thus through the hardness measuring cell is produced by the flow governor. The branched-off mass flow rate can also be controlled via the flow governor.

For automatic operation of the apparatus according to the present disclosure, the hardness measuring cell is provided with a controller by way of which the multiway valve is actuated. If the hardness measuring cell detects a depleted sensor, the multiway valve is actuated in such a way by way of the controller that the measuring device is regenerated and subsequently rinsed. Manual intervention is therefore unnecessary. The controller not only comprises one or more timing elements, but is also equipped with an output for an acoustic, optical and/or electric alarm signal.

Further advantages, features and details of the invention will be apparent from the dependent claims as well as the following description, in which a particularly preferred embodiment is described in detail with reference to the drawings. The features represented in the drawings and mentioned in the claims and in the description can be essential to the invention separately or in any desired combination.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
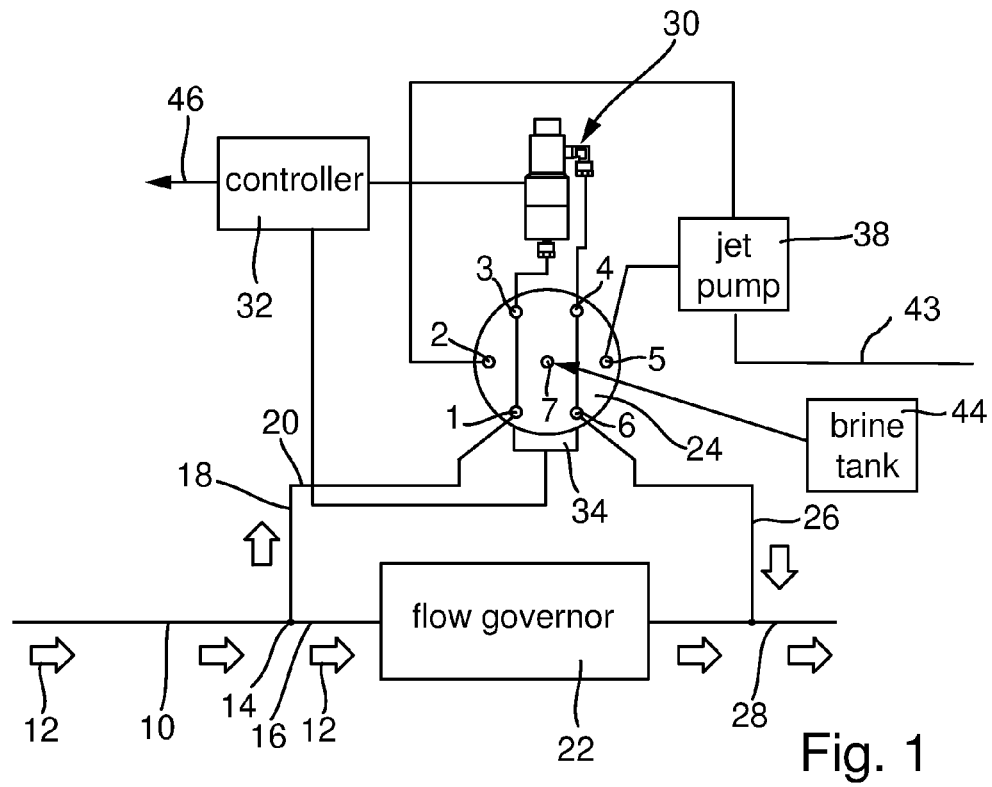
FIG. 1 shows a schematic representation of a measuring distance in normal operation.

A water line for soft water is identified in FIG. 1 with the reference numeral 10 and the flow direction of the soft water is indicated with the arrows 12. The soft water flow is divided at the branch 14 into a main flow 16 and a secondary flow 18 in a secondary flow line 20. A flow governor 22, by which a pressure difference for the flow of the secondary flow 18 is produced, is located in the main flow 16.

Figure 2:
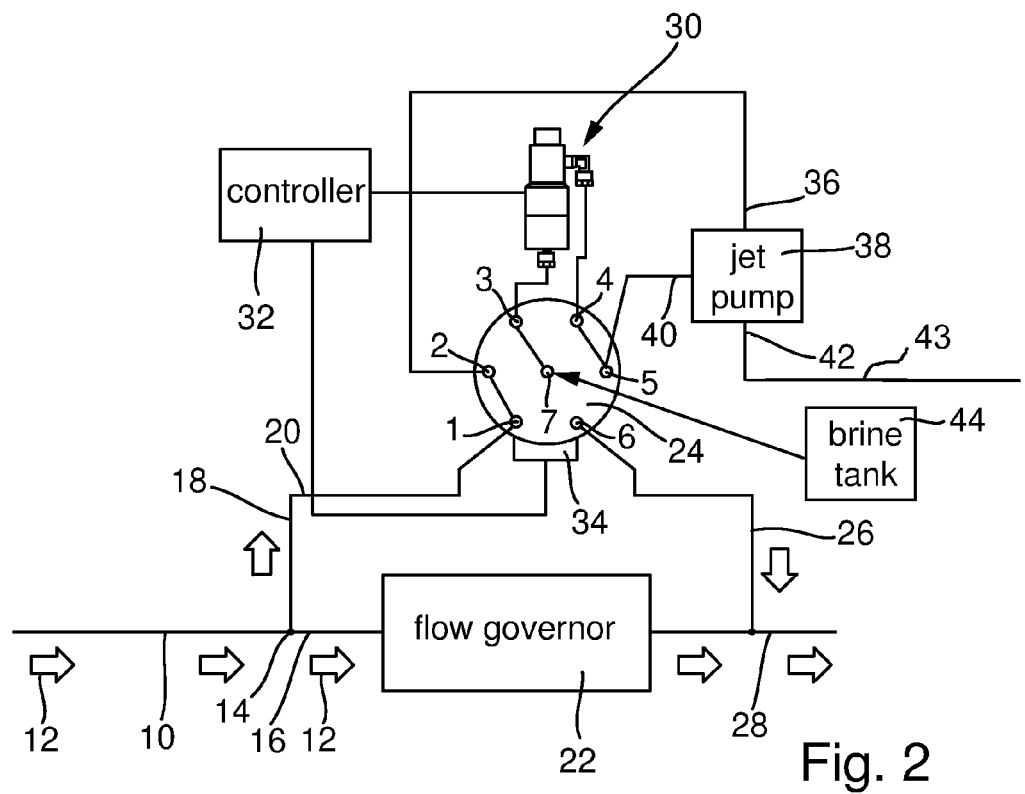
FIG. 2 shows a schematic representation of the measuring distance during regeneration.
Figure 3:
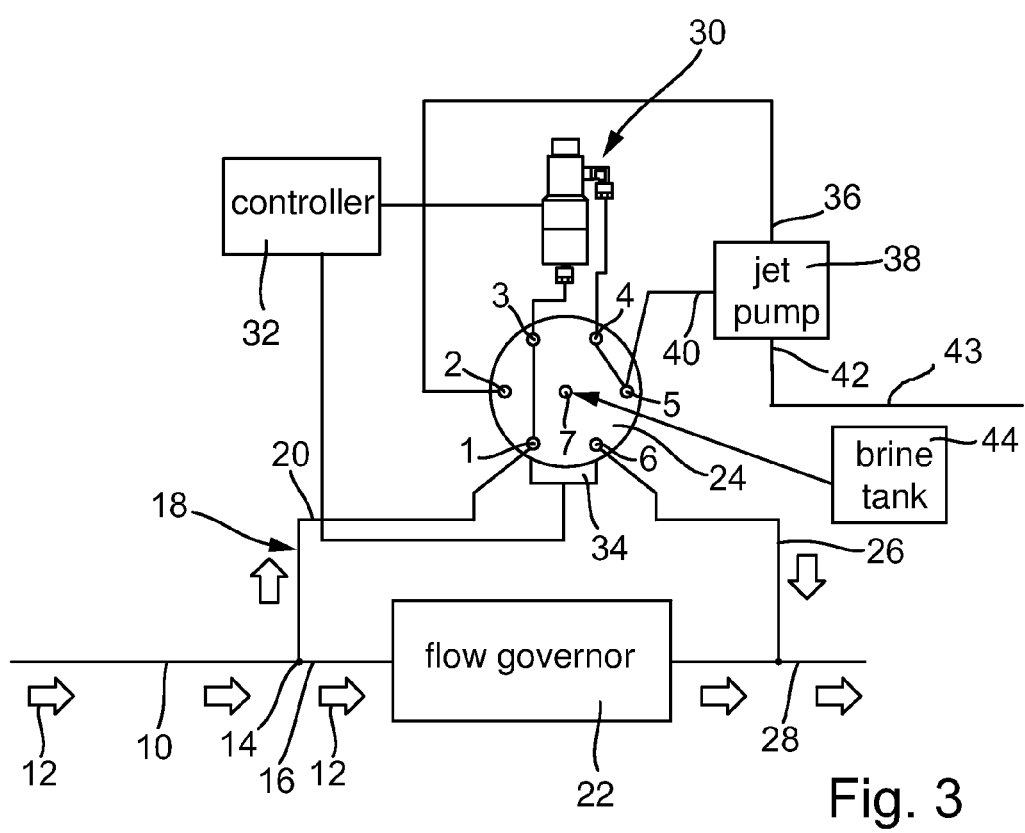
FIG. 3 shows a schematic representation of the measuring distance during the rinsing process.

Also apparent from FIG. 1 is a multiway valve 24, which is configured as a 7/3 valve. The connections of the multiway valve 24 are identified with reference numerals 1 to 7, wherein the three positions of the multiway valve 24 are represented in FIGS. 1 to 3. The secondary flow line 20 is introduced at the connection 1, while a second secondary flow line 26 leads away from the connection 6 and feeds into the main flow 16 downstream of the flow governor 22, so that an outgoing consolidated soft water flow 28 is formed.

A hardness measuring cell 30 can also be seen, the input of which is located at the connection 3 and the output of which is located at the connection 4 of the multiway valve 24. During the normal operation represented in FIG. 1, the connections 1 and 3 and the connections 4 and 6 of the multiway valve 24 are mutually connected, so that the secondary flow 18 flows through the hardness measuring cell 30. The hardness of the soft water is measured in this way.

If hard water flows through the hardness measuring cell 30, then a signal is emitted by the hardness measuring cell 30 to an only schematically represented controller 32, so that suitable measures can be taken, for example, an alarm can be triggered or a system can be deactivated. The controller 32 actuates a drive 34 to adjust the multiway valve 24 for regeneration and the future use of the hardness measuring cell 30.

The multiway valve 24 is adjusted by way of the drive 34 into a position for regeneration of the hardness measuring cell 30. The connections 1 and 2, the connections 3 and 7, as well as the connections 4 and 5 are thus mutually connected. The pressure connection 36 of a water jet pump 38 is located at the connection 2, while the connection 5 is connected to the suction connection 40 for the water jet pump 38. The outlet 42 of the water jet pump 38 leads into a wastewater line 43. Finally, the connection 7 is connected to a brine tank 44.

In this position of the multiway valve 24, the secondary flow 18 drives the water jet pump 38, so that an underpressure is produced at the suction connection 40. This underpressure causes the hardness measuring cell 30 to draw brine from the brine tank 44 via the connections 7 and 3 of the multiway valve 24, so that the sensor located in the hardness measuring cell 30 is regenerated. This brine is then drawn off via the connections 4 and 5 of the multiway valve 24 and combined with the secondary flow 18 of the wastewater line 43 via the outlet 42 of the water jet pump 38. The controller 32 actuates this process within a predeterminable time and switches the multiway valve 24 into the rinsing position after this time has expired.

In FIG. 3, the multiway valve 24 is shown in this position for rinsing the hardness measuring cell 30, wherein the connections 1 and 3 and the connections 4 and 5 are mutually connected in this rinsing position. This means that the secondary flow 18 is fed via the connections 1 and 3 to the hardness measuring cell 30, so that this secondary flow 18 flows through the hardness measuring cell 30 and all of the brine located in the hardness measuring cell 30 is fed via the connections 4 and 5 of the multiway valve 24 to the suction connection 40 of the water jet pump 38, which is not in operation in this position of the multiway valve 24, so that the fluid can be fed via the outlet 42 of the water jet pump 38 to the wastewater line 43. After a second predeterminable time period has expired, the drive 34 is actuated by way of the controller 32 and the multiway valve 24 is switched into the position for normal operation of the hardness measuring cell 30, which is shown in FIG. 1. The soft water can now be monitored again.

The apparatus according to one form of the present disclosure operates fully automatically and emits, for example, an alarm signal 46 in a suitable way via the controller 12, for example, as an optical, acoustic or electric signal, when hard water is detected. Suitable measures can be taken fully automatically. Even if the sensor has to be routinely regenerated, this can be carried out via the controller 12.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. An apparatus for monitoring soft water fed into a water line, comprising a hardness measuring cell connected in parallel to a main flow, a first secondary flow line branching off from the main flow and leading to the hardness measuring cell, and a second secondary flow line leading away from the hardness measuring cell and feeding into the main flow, characterized in that the two secondary flow lines and the hardness measuring cell are connected to a multiway valve,
    characterized in that the multiway valve is a 7/3 valve having seven connections and three switching positions.

2. The apparatus according to claim 1, characterized in that a water jet pump is connected to the multiway valve.

3. The apparatus according to claim 2, characterized in that an outlet of the water jet pump is connected to a wastewater line.

4. The apparatus according to claim 1, characterized in that the multiway valve is connected to a brine tank.

5. The apparatus according to claim 1, characterized in that the hardness measuring cell is connected to a controller, by way of which the multiway valve is actuated.

6. The apparatus according to claim 5, characterized in that the controller drives a drive that actuates the multiway valve.

7. An apparatus for monitoring soft water fed into a water line, comprising a hardness measuring cell connected in parallel to a main flow, a first secondary flow line branching off from the main flow and leading to the hardness measuring cell, and a second secondary flow line leading away from the hardness measuring cell and feeding into the main flow, characterized in that the two secondary flow lines and the hardness measuring cell are connected to a multiway valve, characterized in that a flow governor is provided in the main flow and between the branchings of the secondary flow lines.

* * * * *